(12) United States Patent
Burnes

(10) Patent No.: US 6,931,272 B2
(45) Date of Patent: Aug. 16, 2005

(54) METHOD AND APPARATUS TO MONITOR PULMONARY EDEMA

(75) Inventor: John E. Burnes, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 116 days.

(21) Appl. No.: 10/426,978

(22) Filed: Apr. 29, 2003

(65) Prior Publication Data

US 2004/0220632 A1 Nov. 4, 2004

(51) Int. Cl.[7] .................................................. A61B 5/04
(52) U.S. Cl. .......................... 600/509; 607/3; 600/547
(58) Field of Search ....................... 607/3, 28; 600/509, 600/547

(56) References Cited

U.S. PATENT DOCUMENTS

| | | |
|---|---|---|
| 3,821,948 A | 7/1974 | King |
| 5,456,261 A | 10/1995 | Luczyk ....................... 128/702 |
| 5,876,353 A | 3/1999 | Riff |
| 5,904,708 A | 5/1999 | Goedeke |
| 5,957,861 A | 9/1999 | Combs et al. |
| 6,473,640 B1 * | 10/2002 | Erlebacher ................... 600/547 |

OTHER PUBLICATIONS

Madias, et al., *Anasarca–Mediated Attenuation of the Amplitude of Electrocardiogram Complexes: A Description of a Heretofore Unrecognized Phenomenon*, vol. 38, No. 3, 2001, Journal of American College of Cardiology.

* cited by examiner

Primary Examiner—Mark Bockelman
(74) Attorney, Agent, or Firm—Paul H. McDowall; Girma Wolde-Michael

(57) ABSTRACT

In general, the invention is directed to monitoring fluid retention that may accompany congestive heart failure and pulmonary edema. A medical device, such as an implanted pacemaker or an external defibrillator, senses electrical signals associated with the periodic depolarization and re-polarization of a heart. The device processes the electrical signals to obtain one or more "cardiac parameters," which reflect pulmonary edema. By monitoring the cardiac parameters, the device monitors pulmonary edema. Cardiac parameters comprise the amplitude of the QRS complex, the integral of the QRS complex, or the integral of the QRST segment and the like. When the device detects fluid buildup, the device may respond by taking remedial action and/or generating an alert.

28 Claims, 4 Drawing Sheets

METHOD AND APPARATUS TO MONITOR PULMONARY EDEMA

CROSS REFERENCE TO RELATED APPLICATIONS

This patent disclosure hereby incorporates by reference the following patent applications filed on even date hereof; namely, Ser. No. 10/426,645, "Cardiac Pacing Therapy Parameter Programming;" Ser. No. 10/426,613, "Method and Apparatus for Detecting Myocardial Electrical Recovery and Controlling Extra-Systolic Stimulation;" Ser. No. 10/426,613, "Method and Apparatus for Determining Myocardial Electrical Resitution and Controlling Extra Systolic Stimulation;" and Ser. No. 10/426,644, "Use of Activation and Recovery Times and Dispersions to Monitor Heart Failure Status and Arrhythmia Risk."

TECHNICAL FIELD

The invention relates to medical devices, and more particularly, to medical devices that sense cardiac electrical signals.

BACKGROUND

Heart failure refers to the heart's inability to keep up with the demands made upon it. Congestive heart failure refers to an inability of the heart to pump an adequate amount of blood to the body tissues. Because the heart is unable to pump an adequate amount of blood, blood returning to the heart becomes congested in the venous system.

In a healthy heart, the heart pumps all of the blood that returns to it, according to the Frank-Starling law. Increased venous return leads to increased end diastolic volume, which causes increased strength of contraction and increased stroke volume. In addition to intrinsic control according to the Frank-Starling law, a healthy heart is subject to extrinsic control, such as stimulation by the sympathetic nervous system to enhance contractility.

In a patient experiencing congestive heart failure, intrinsic and extrinsic control mechanisms may not function properly, and consequently the heart may fail to pump an adequate amount of blood. Failure of the left side of the heart is generally more serious than the failure of the right side. On the left side of the heart, blood returns from the pulmonary system and is pumped to the rest of the body. When the left side of the heart fails, there are consequences to both the pulmonary system and to the rest of the body. A patient with congestive heart failure may be unable to pump enough blood forward to provide an adequate flow of blood to his kidneys, for example, causing him to retain excess water and salt. His heart may also be unable to handle the blood returning from his pulmonary system, resulting in a damming of the blood in the lungs and increasing his risk of developing pulmonary edema.

Some patients with congestive heart failure benefit from an implanted pacemaker. A pacemaker rhythmically generates impulses that spread throughout the heart to drive the atria and ventricles. A typical pacemaker monitors the electrical activity of the patient's heart and provides pacing to cause the heart to beat (i.e., depolarize) at a desired rate. Patients having electrical-mechanical dysynchrony may receive benefits from a pacemaker that provides cardiac resynchronization, i.e., that paces both ventricles or both atria to improve synchrony.

A rate-responsive pacemaker adjusts the pacing rate to the changing needs of the patient. For example, a rate-responsive pacemaker may normally pace the patient at sixty beats per minute when the patient is sleeping or at rest. When the patient increases his activity, however, the pacemaker may pace the patient's heart more rapidly to produce a higher heart rate.

SUMMARY

In general, the invention is directed to monitoring fluid retention that may accompany congestive heart failure and pulmonary edema. A medical device, such as an implanted pacemaker that records an electrogram (EGM) or an external or subcutaneous device that records an electrocardiogram (ECG), senses electrical signals associated with depolarization and repolarization of the heart. The device processes the electrical signals to obtain one or more "cardiac parameters," which will be described below. The cardiac parameters reflect fluid retention within the lungs. Accordingly, the device can monitor pulmonary edema by monitoring one or more cardiac parameters.

Cardiac parameters are a function of the QRS complex or the QRST segment. When a heart undergoes a normal cardiac cycle, the ECG or EGM include a QRS complex and a T-wave. The QRS complex is typically a narrow wave indicative of ventricular depolarization, and the T-wave is a more gradual wave indicative of ventricular re-polarization. When the patient experiences increasing fluid in the lungs, the impedance of the body of the patient declines. As a result, the amplitudes of the QRS complex and the T-wave generally become smaller over several cardiac cycles.

The invention provides for monitoring at least one "cardiac parameter," defined as the amplitude of the QRS complex, the integral of the QRS complex, or the integral of the QRST segment. Each of these cardiac parameters reflects the change in patient impedance that accompanies a buildup of fluid in the lungs. Accordingly, the invention provides for monitoring pulmonary edema in the lungs as a function of the cardiac parameter.

When a medical device detects fluid buildup, the device may respond by taking remedial action. For example, the device may generate an alert to notify the patient, so that the patient may take a medication or seek medical attention. In the case of a medical device that is configured to deliver pacing stimuli to the heart, the device may increase the pacing rate. Increasing the pacing rate increases the cardiac output, and may reduce the damming of the blood responsible for the fluid buildup. It is also possible that the medical device may control a drug pump, which administers a drug to the patient to alleviate the fluid retention.

In one embodiment, the invention is directed to a method comprising monitoring at least one cardiac parameter over a plurality of cardiac cycles, and monitoring pulmonary edema in a patient as a function of the monitored cardiac parameter. The cardiac parameter can include an amplitude of a QRS complex generated by a heart, an integral of the QRS complex, or an integral of a QRST segment. The method can further include taking remedial action in response to the monitoring of the cardiac parameter, such as delivering pacing stimuli to the heart, delivering a drug to the patient, controlling a device to deliver therapy to the patient and generating an alert.

In another embodiment, the invention includes a computer-readable medium comprising instructions for causing a programmable processor to carry out this method.

In a further embodiment, the invention is directed to a device comprising a sensor to sense electrical signals from a heart of a patient, and a processor to receive the electrical signals and to monitor at least one cardiac parameter over a plurality of cardiac cycles. The processor is further configured to monitor pulmonary edema in a body of a patient as a function of monitoring the cardiac parameter. The device may also include an implantable pulse generator to deliver pacing therapy to the heart, a drug pump or an output device to generate an alert. The device may be implanted or external or a combination of implanted and external components.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
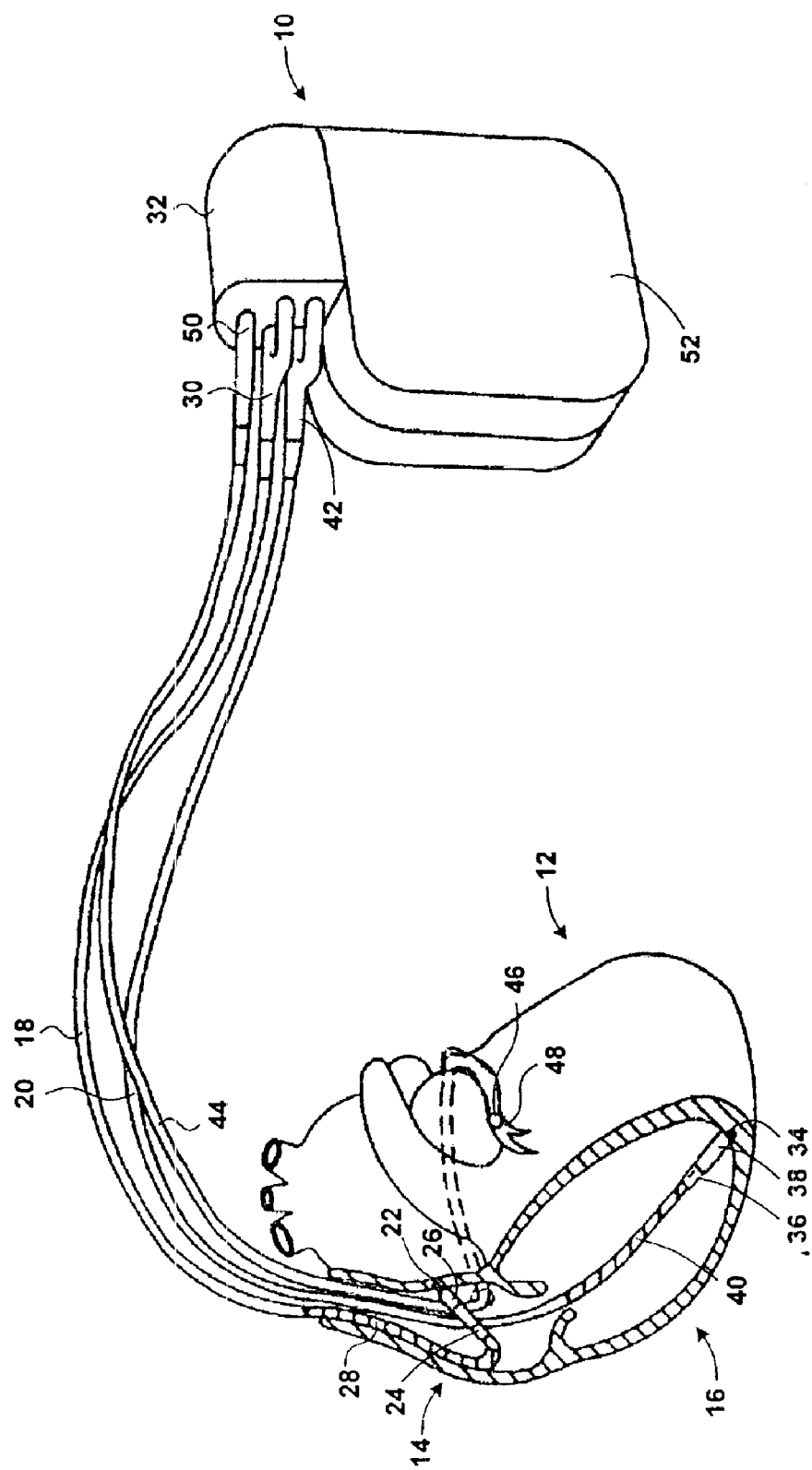
FIG. 1 is a schematic illustration of an exemplary implantable medical device that practices the invention, with a human heart.

FIG. 1 depicts an exemplary implantable medical device (IMD) 10 that may practice the techniques of the invention. In the example of FIG. 1, IMD 10 is an implantable multi-chamber pacemaker that includes cardioversion and defibrillation capability. The invention is not limited to the particular IMD shown in FIG. 1, however, but may be practiced by any number of implantable devices. The techniques of the invention may be practiced by a device that paces a single cardiac chamber or several chambers, that paces one or more atria or one or more ventricles, and that paces in any of several pacing modes. As will be described below, the techniques of the invention may be also be practiced by subcutaneous and external devices, or any combination of implanted, subcutaneous of external components.

IMD 10 includes an implantable pulse generator (IPG) (not shown in FIG. 1) that generates pacing stimuli to administer one or more pacing therapies to heart 12. Pacing stimuli may be applied to the right atrium 14, for example, or the right ventricle 16, or both. IMD 10 also includes circuitry to sense atrial and ventricular activations. Atrial and ventricular bipolar pace/sense electrode pairs at the distal ends of leads 18 and 20, respectively, carry out the pacing and sensing functions.

In right atrium 14, the distal end of atrial lead 18 includes an extendable helical, pace/sense tip electrode 22 and a pace/sense ring electrode 24. Helical electrode 22 extends from electrode head 26 into the atrial appendage. Pace/sense electrodes 22 and 24 are employed for atrial pacing and for sensing of P-waves indicative of atrial activation. The distal end of atrial lead 18 also includes an elongated coil defibrillation electrode 28 that can deliver a defibrillation shock to right atrium 14. Electrode 28 may also be used to deliver cardioversion therapy to right atrium 14.

Atrial lead 18 may include conductors that electrically couple electrodes 22, 24 and 28 to IMD 10. The conductors may be arranged coaxially, coradially, in parallel, or in another configuration, and may be insulated from one another and from the tissue of the patient. The proximal end of atrial lead 18 may include a bifurcated connector 30 that couples the conductors to a connector block 32 on IMD 10.

In right ventricle 16, the distal end of ventricular lead 20 likewise may include a pace/sense tip electrode 34 and a pace/sense ring electrode 36. Pace/sense tip electrode 34 may be a helical electrode that extends from electrode head 38 toward the apex of heart 12. Pace/sense electrodes 34 and 36 are employed for ventricular pacing and for sensing of R-waves indicative of ventricular activation. The distal end of ventricular lead 20 also includes an elongated coil defibrillation electrode 40 that can deliver a defibrillation shock or cardioversion therapy to right ventricle 16.

Like atrial lead 18, ventricular lead 20 may include one or more insulated conductors that electrically couple electrodes 34, 36 and 40 to IMD 10. The proximal end of ventricular lead 20 may include a bifurcated connector 42 that couples the conductors to connector block 32.

FIG. 1 illustrates deployment of a coronary sinus lead 44. Coronary sinus lead 44 may include one or more insulated conductors. The proximal end of coronary sinus lead 44 may include one or more electrodes, such as pace/sense electrode 46. Pace/sense electrode 46 may be deployed within the great vein 48 of heart 12, and may be used to deliver pacing therapies to the left side of heart 12. A connector 50 at the proximal end of the coronary sinus lead 44 couples the conductors in lead 44 to connector block 32. In some embodiments of the invention, coronary sinus lead 44 may include an elongated exposed coil wire defibrillation electrode (not shown).

IMD 10 includes a housing 52 that serves as a "can" electrode. In unipolar pacing operations, IMD 10 may deliver an electrical stimulation to heart 12 via an electrode disposed on one or more of leads 18, 20 or 44, with housing 52 being a part of the return current path. In bipolar pacing operation, by contrast, IMD 10 may deliver an electrical stimulation to heart 12 via a tip electrode, with a ring electrode providing the principal return current path. In some embodiments of the invention, housing 52 includes two electrodes, and IMD 10 may detect electrical signals generated by heart 12 with electrodes disposed in housing 52.

IMD 10 is configured to monitor the changes in thoracic impedance between any of electrodes 18, 20, 44 and housing 52, by monitoring the electrical signals generated by heart 12. In particular, IMD 10 monitors the QRS complex, with or without the T-wave. When the patient's impedance changes due to fluid in the lungs and within the tissues of the thorax, the amplitudes of the QRS complex and the T-wave generally change as well. IMD 10 includes a processor (not shown in FIG. 1) that analyzes the QRS complex or QRST segment to monitor fluid retention. In particular, IMD 10 monitors at least one "cardiac parameter," defined as the amplitude of the QRS complex, the integral of the QRS complex, or the integral of the QRST segment.

Each of these cardiac parameters reflects the change in patient impedance that accompanies a buildup of fluid in the lungs. In particular, the impedance varies as a function of pulmonary edema or fluid in the lungs or "lung wetness." Generally speaking, increased lung wetness decreases the impedance between an electrode deployed in heart 12 and the can electrode of housing 52.

A surgeon may implant housing 52 at a site in the body of the patient such that lung tissue is interposed between housing 52 and heart 12. With such an implantation, fluid in the lungs is more likely to affect the impedance of the current path between an electrode deployed in heart 12 and the can electrode of housing 52. As a result, the changes to the cardiac parameters that accompany a change in lung fluid are more likely to be pronounced and are more likely to be easily detected. However, implantable loop recorder (ILR) devices such as those manufactured by Medtronic, Inc. of Minneapolis, Minn. typically operate with surface mount electrodes disposed about a unitary canister and other types of electrodes (e.g., subcutaneous electrode array, pericardial electrodes, epicardial electrodes, and the like) may be used in conjunction with the present invention.

Figure 2:
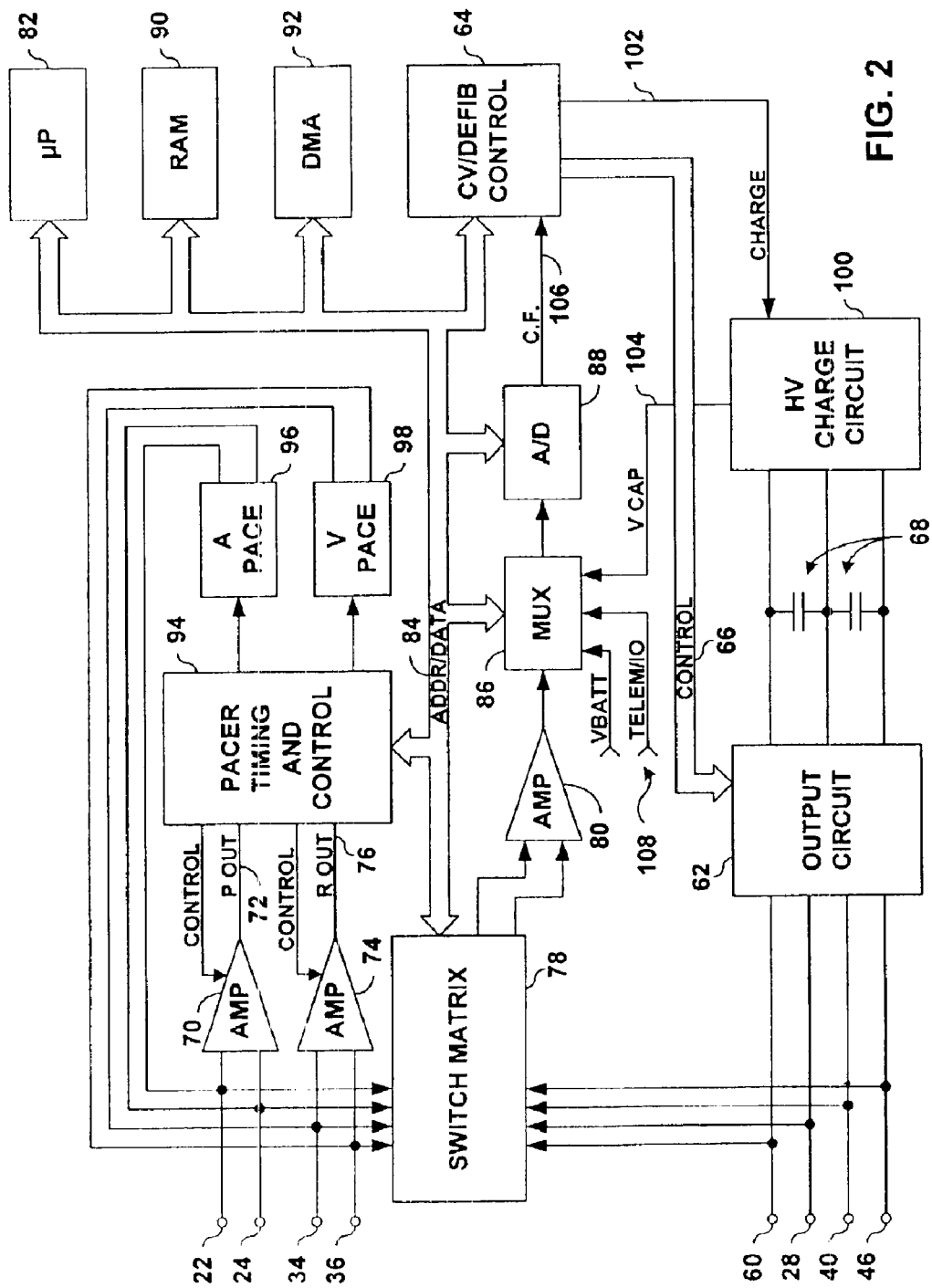
FIG. 2 is a block diagram illustrating the operation of the embodiment of the implantable medical device shown in FIG. 1.

FIG. 2 is a functional schematic diagram of one embodiment of IMD 10. FIG. 2 illustrates how IMD 10 detects fluid in the lungs and responds to fluid in the lungs. This diagram is exemplary of the type of device in which various embodiments of the invention may be embodied, and the invention is not limited to the particular schematic shown. On the contrary, the invention may be practiced in a wide variety of devices, including single-and multi-chamber devices.

FIG. 2 includes electrode terminals 22, 24, 28, 34, 36, 40 and 46, which correspond to the electrodes shown in FIG. 1. Electrode 60 corresponds to the uninsulated portion of housing 52 of IMD 10. In some embodiments, housing 52 may include a second electrode (not shown). Electrodes 28, 40 and 46 are coupled to high voltage output circuit 62, which includes high voltage switches controlled by cardioversion/defibrillation (CV/defib) control logic 64 via control bus 66. Switches disposed within circuit 62 determine which electrodes are employed and which electrodes are coupled to the positive and negative terminals of a capacitor bank 68 during delivery of defibrillation or cardioversion shocks.

Electrodes 22 and 24, located on or in right atrium 14, are coupled to a P-wave amplifier 70. Amplifier 70 may comprise an automatic gain controlled amplifier providing an adjustable sensing threshold as a function of the measured P-wave amplitude. Amplifier 70 generates a signal on P-out line 72 whenever the signal sensed between electrodes 22 and 24 exceeds the sensing threshold.

Electrodes 34 and 36, located in right ventricle 16, are coupled to an R-wave amplifier 74. Amplifier 74 may comprise an automatic gain controlled amplifier providing an adjustable sensing threshold as a function of the measured R-wave amplitude. Amplifier 74 generates a signal on R-out line 76 whenever the signal sensed between electrodes 34 and 36 exceeds the sensing threshold of amplifier 74.

A switch matrix 78 selects electrodes for coupling to a wide band amplifier 80 for use in digital signal analysis. Selection of electrodes is controlled by microprocessor 82 via data/address bus 84. As shown in FIG. 2, microprocessor 82 can control switch matrix 78 to select any of pace/sense electrodes 22, 24, 34, 36, and any of defibrillation electrodes 28, 40, 46, and can electrode 60. In this way, microprocessor 82 controls which electrodes are selected as sensors to sense electrical signals from heart 12.

The signals from the selected electrodes are provided to multiplexer 86, and are thereafter converted to multi-bit digital signals by A/D converter 88. The signals may be stored in random access memory (RAM) 90 under control of direct memory access (DMA) circuit 92. Microprocessor 82 selects the electrodes used as sensors to sense cardiac electrical signals, further processes the signals to monitor one or more cardiac parameters.

Digital signal analysis includes, but is not limited to, analysis of the electrical signals sensed via the selected electrodes, and may include operations such as amplifying, rectifying, filtering, summing and integrating. Digital signal analysis also may include morphological analysis, such as analysis employing wavelet, Fourier or similar spectral analysis techniques.

In particular, digital signal analysis includes determination of at least one cardiac parameter. Microprocessor 82 measures the amplitude of the QRS complex, or the integral of the QRS complex, or the integral of the QRST segment. The QRS complex or QRST segment may be rectified prior to measurement. In a typical application, microprocessor 82 selects the signal sensed between can electrode 60 and a defibrillation coil electrode 28, 40 or 46, and evaluates the QRS complex or QRST segment of the signal sensed by the selected electrodes. Microprocessor 82 may also select the signal sensed between two can electrodes.

As lung wetness increases, the impedance along the current path declines. The change in impedance manifests as a decline in the amplitude of the QRS complex, and a decline in the amplitude of the T-wave. Microprocessor 82 may detect the change in impedance by detecting the change in a QRS amplitude, such as the peak-to-peak amplitude. The change in impedance also manifests as a change to the integral of the QRS complex, or a change to the integral of the QRST segment. In particular, as the QRS amplitude declines, the integral represented by the area under the curve also declines. Consequently, microprocessor 82 may detect the change in impedance by detecting the change in the integral of the QRS complex, or the change to the integral of the QRST segment.

In other words, the amplitude of the QRS complex, the integral of the QRS complex, or the integral of the QRST segment are cardiac parameters that reflect thoracic impedance, which in turn reflect lung wetness. Microprocessor 82 may monitor any or all of the cardiac parameters to monitor changes in lung wetness. The cardiac parameters are not exclusive of one another. Microprocessor 82 or discrete circuitry may, for example, apply low-pass filtering to the QRS complex or the QRST segment, which effectively combines integration with other mathematical operations. Microprocessor 82 may also apply a digital summing operation that approximates or substantially integrates the QRS complex or the QRST segment. The "integral" of a QRS complex or QRST segment includes all of these variations.

By monitoring one or more of these cardiac parameters, IMD 10 is able to detect fluid retention early, before pulmonary edema becomes a serious problem for the patient. In addition, IMD 10 may apply one or more therapies in response to the monitoring of the cardiac parameter. IMD 10 may, for example, pace heart 12 to alleviate fluid in the lungs.

In typical conditions, IMD 10 uses signals sensed via electrodes 22, 24, 34 and 36 to determine whether to administer cardiac pacing, cardioversion or defibrillation therapies. Pacer timing/control circuitry 94 receives signals from P-out line 72 and R-out line 76, and computes various timing intervals as a function of the timing of the received signals. Pacer timing/control circuitry 94 also may include programmable digital counters that control pacing according to any of several pacing modes. Pacer output circuitry 96 and 98, which are coupled to electrodes 22, 24, 34 and 36, generate pacing stimuli under the control of pacer timing/control circuitry 94. The IPG of IMD 10 comprises microprocessor 82, in cooperation with pacer timing/control circuitry 94 and pacer output circuitry 96 and 98.

When IMD 10 detects one or more monitored cardiac parameters that indicate that the patient is experiencing lung wetness, IMD 10 may apply cardiac pacing to alleviate the pulmonary edema. For example, when IMD 10 detects a cardiac parameter indicative of high lung wetness, microprocessor 82 may select a pacing regimen that increases the heart rate and thereby increases cardiac output. By delivering pacing stimuli to increase cardiac output, IMD 10 delivers pacing stimuli to pump more blood and alleviate the damming of the blood in the lungs due to inadequate cardiac output. In this way, IMD 10 reduces the risk to the patient of pulmonary edema.

As noted above, defibrillation coil electrodes 28, 40 and 46 may be used to sense cardiac parameters. Defibrillation coil electrodes 28, 40 and 46 may also be used to administer defibrillation and cardioversion therapies.

When a cardioversion or defibrillation pulse is required, microprocessor 82 may control the timing, strength and duration of cardioversion and defibrillation pulses. In response to the detection of atrial or ventricular fibrillation or tachycardia requiring a cardioversion pulse, microprocessor 82 activates CV/defib control circuitry 64, which initiates charging of capacitor bank 68 via charging circuit 100, under the control of high voltage charging control line 102. The voltage on the high voltage capacitors is monitored via VCAP line 104, which is passed through multiplexer 86, and in response to reaching a predetermined value set by microprocessor 82, results in generation of a logic signal on Cap Full (CF) line 106 to terminate charging. A defibrillation or cardioversion pulse may be delivered by output circuit 62.

IMD 10 includes one or more telemetry units 108 that support communication with one or more other devices. Telemetry unit 108 may, for example, support wireless communication with another implantable medical device, such as a drug pump. When IMD 10 detects one or more monitored cardiac parameters that indicate that the patient is experiencing lung wetness, IMD 10 may send a signal via telemetry unit 108 to the drug pump to administer a drug that alleviates the fluid retention. The drug may enhance heart contractility, for example, thereby increasing cardiac output, or administer a drug that initiates diuresis, thereby reducing patient fluid. In other words, IMD 10 may address fluid in the lungs with therapy other than pacing therapy.

IMD 10 may further wirelessly communicate with an external device via telemetry unit 108. IMD 10 may upload data via telemetry unit 108 and may also download data and programming via telemetry unit 108. In addition, IMD 10 may generate an alert when the patient is experiencing lung wetness, and may communicate the alert to the external device. The external device in turn may notify the patient with a visual or audible signal, or forward the alert to a remote location such as the office of a physician caring for the patient. Telemetry unit 108 may communicate wirelessly with the external device via radio frequency communication, magnetic communication, ultrasound communication or any other communication technique.

In addition, IMD 10 may include a component (not shown) that provides a sensory alert signal to the patient. The alert signal may include a vibration or an audible tone. IMD 10 may activate this component to notify the patient of fluid in the lungs. Notified of the condition, the patient may take a medication to alleviate the fluid in the lungs.

Figure 3:
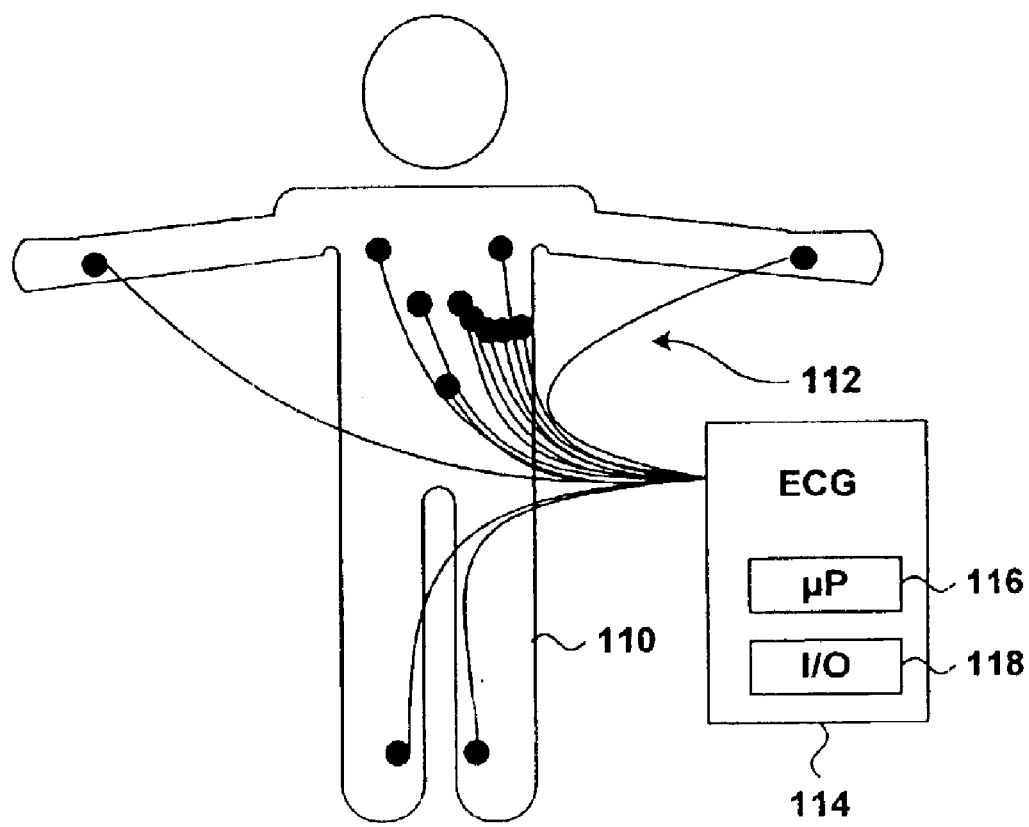
FIG. 3 is schematic illustration of an exemplary external medical device that practices the invention, with a patient.

FIG. 3 is a schematic illustration of another embodiment of the invention, in which the medical device is external rather than implanted. In FIG. 3, patient 110 is coupled via multiple leads 112 to an electrocardiogram (ECG) apparatus 114 deployed in a standard fashion. ECG apparatus 114 receives electrical signals from leads 112, including the QRS complex and T-wave.

A microprocessor 116 in ECG apparatus 114 monitors one or more cardiac parameters by applying the techniques described above. In particular, microprocessor 116 receives cardiac signals sensed via leads 112 and monitors at least one of the amplitude of the QRS complex, the integral of the QRS complex, or the integral of the QRST segment. Each of these cardiac parameters reflect body impedance, which in turn reflect fluid in the lungs. ECG apparatus 114 includes an input/output (I/O) device 118 that alerts a person when ECG apparatus 114 detects cardiac parameters that indicate patient 110 may need therapy to alleviate fluid in the lungs. I/O device 118 may be, for example, an audible alarm that notifies an operator of the condition of patient 110, or a device that downloads data about the condition of patient 110 to a remote location such as the office of a physician caring for patient 110.

ECG apparatus 114 may, but need not, administer the therapy itself or control administration of the therapy. In one embodiment of the invention, ECG apparatus 114 may comprise an external defibrillator or external pacemaker configured to apply external pacing stimuli to increase cardiac output. In that embodiment, lead system 112 may include more or fewer leads than are depicted in FIG. 3, and the electrodes on the distal ends of the leads need not be disposed proximate to the heart in exactly the same way as shown in FIG. 3. Moreover, the same leads that sense cardiac electrical activity may also deliver pacing stimuli. In another embodiment of the invention, ECG apparatus 114 may control an external or internal drug pump to administer a medication to increase cardiac output or increase fluid diuresis.

Figure 4:
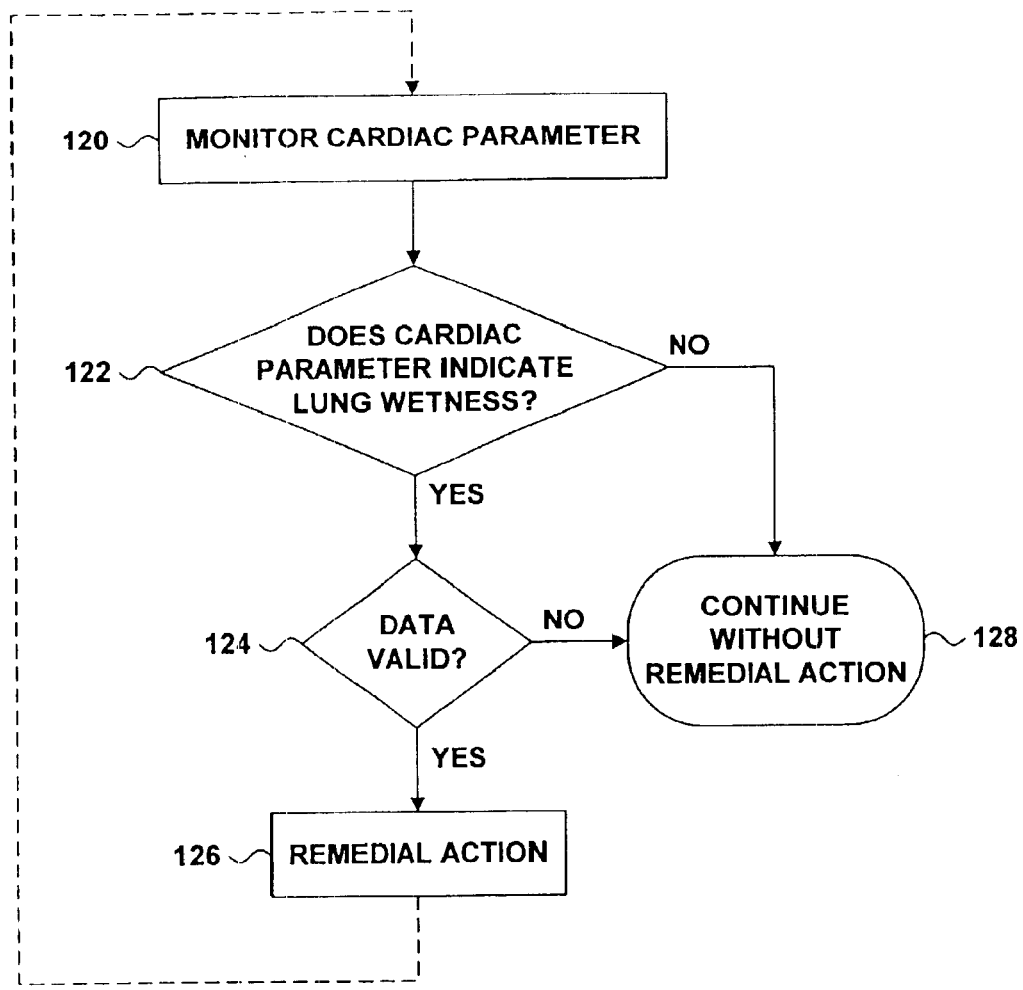
FIG. 4 is a flow diagram illustrating techniques for monitoring fluid in the lungs by monitoring one or more cardiac parameters.

FIG. 4 is a flow diagram illustrating an method for carrying out the invention. The techniques shown in FIG. 4 may be applied by IMD 10, external ECG apparatus 114, or by another internal, external or subcutaneous medical device. The device monitors a cardiac parameter (120) as described above. In particular, the device monitors the amplitude of a QRS complex, an integral of the QRS complex, or an integral of a QRST segment. The device also monitors pulmonary edema in the patient as a function of monitoring the cardiac parameter (122).

The device typically compares one or more current cardiac parameters to past cardiac parameters to determine whether the cardiac parameters indicate fluid in the lungs. In other words, the device may determine that the patient is experiencing fluid in the lungs when the cardiac parameter changes over several cardiac cycles. The cardiac cycles may be separated by any time interval. As fluid accumulates in the chest, the amplitudes of the QRS complex and the T-wave generally become smaller over time, and the integrals or "areas under the curve"decline as well.

When the change in cardiac parameter surpasses a predetermined threshold, the device may determine that the patient is experiencing fluid in the lungs, and may benefit from medical attention or therapy. When, for example, the QRS integral declines by a predetermined percentage, such as five percent or another programmed percentage, the device may determine that fluid in the lungs is indicated.

It is possible that some changes to cardiac parameters are not indicative of lung wetness. For example, a QRS complex resulting from an intrinsic ventricular activation may be of a different amplitude than a QRS complex resulting from a ventricular pace. In those circumstances, a change in cardiac parameter is not indicative of lung wetness. Also, a premature ventricular contraction (PVC) or other irregularity may cause the device to determine that there has been a change in one or more cardiac parameters, but the change is not indicative of lung wetness.

Accordingly, the device typically performs data validation (124) to determine whether the change in cardiac parameters is due to lung wetness or other factors. In IMD 10, for example, microprocessor 82 typically distinguishes sensed ventricular beats from paced beats, and further includes algorithms for distinguishing normal from irregular cardiac cycles.

When there has been a change in one or more cardiac parameters, and the change has been validated, then the device may take remedial action (126). The remedial action may include the application of therapy, such as pacing to increase cardiac output, or the control of a therapy device, such as drug pump, or the generation of an alert. When the remedial action includes therapy to alleviate fluid in the lungs, the device may monitor the progress of the therapy by monitoring the cardiac parameter (120).

When there has not been a significant change in the cardiac parameters, or when data validation (124) indicates the change is attributable to factors other than fluid in the lungs, or when the cardiac parameters indicate that therapy has alleviated fluid in the lungs, the device may continue operation without taking remedial action (128). The device may continue monitoring (120), for example, or may report that the patient does not suffer from lung wetness.

The preceding specific embodiments are illustrative of the practice of the invention. Various modifications may be made without departing from the scope of the claims. For example, the invention is not limited to practice with the particular the medical devices described herein. The invention may be practiced, for example, with an implantable recorder that monitors the heart but does not include therapeutic capability. Nor is the invention limited to any particular number of electrodes or to any placement of the electrodes proximate to the heart.

The invention includes embodiments of the invention in which a device measures the impedance of the patient directly. The invention includes embodiments in which the device, for example, delivers a known current to the body via two or more electrodes and measures the voltage that develops between the electrodes. Direct measurements of impedance, however, are affected by factors other than lung wetness, such as respiration, and additional signal processing may be needed to isolate the impedance signals of interest. Monitoring of the QRS complex or QRST segment in many cases provides an indication of fluid in the lungs that is more efficient and reliable as direct impedance measurement.

The invention is not limited to monitoring of the QRS complex or QRST segment as sensed by a single pair of electrodes. On the contrary, a device may take multiple signals from multiple electrode configurations when monitoring fluid in the lungs. Amplitudes, derivatives and/or integrals from a plurality of signals may be added or otherwise processed when monitoring lung wetness.

Monitoring of the QRS complex or QRST segment may be useful for purposes other than monitoring fluid in the lungs. For example, a widening of the QRS complex may indicate ventricular dysynchrony, heart failure or a risk of sudden cardiac death. The invention does not interfere with monitoring of the QRS complex or QRST segment for any other purpose, but cooperates with other techniques. A device may employ morphological or other analysis to distinguish whether a change in the QRS integral is caused by a change in the QRS amplitude, for example, or whether the change in the QRS integral is caused by a change in the QRS width.

Some of the techniques described above may be embodied as a computer-readable medium comprising instructions for a programmable processor. Examples of programmable processors include microprocessor 82 and pacer timing/ control circuitry 94 of IMD 10 shown in FIG. 2, and microprocessor 116 of ECG apparatus 114 depicted in FIG. 3. The programmable processor may include one or more individual processors, which may act independently or in concert. A "computer-readable medium" includes but is not limited to read-only memory, Flash memory and a magnetic or optical storage medium. The medium may comprise instructions for causing a programmable processor to monitoring at least one cardiac parameter and monitor pulmonary edema in a patient as a function of monitoring the cardiac parameter. These and other embodiments are within the scope of the following claims.

What is claimed is:

1. A method comprising:
   monitoring a cardiac parameter over a plurality of cardiac cycles, the cardiac parameter comprising at least one of:
   an amplitude of a QRS complex generated by a heart;
   an integral of the QRS complex,
   an integral of a QRST segment; and
   monitoring a pulmonary edema status of a patient as a function of the monitored cardiac parameter.

2. A method according to claim 1, further comprising taking a remedial action in response to the monitoring of the cardiac parameter.

3. A method according to claim 2, wherein taking remedial action comprises at least a one of:
   delivering pacing stimuli to the heart;
   delivering a drug to the patient;
   controlling a device to deliver therapy to the patient;
   generating an audible, tactile, visual alert signal.

4. A method according to claim 2, further comprising:
   comparing a change in the monitored cardiac parameter to a threshold; and
   taking the remedial action when the monitored cardiac parameter surpasses the threshold.

5. A method according to claim 1, further comprising monitoring at least one cardiac parameter over a second plurality of cardiac cycles.

6. A method according to claim 1, further comprising evaluating the monitored cardiac parameter to determine whether a change in the monitored cardiac parameter indicates a change in pulmonary edema.

7. A computer-readable medium comprising instructions for causing a programmable processor to:
   monitor a cardiac parameter over a plurality of cardiac cycles, the cardiac parameter comprising at least one of
   an amplitude of a QRS complex generated by a heart,
   an integral of the QRS complex, and an integral of a QRST segment; and
   monitor pulmonary edema in a patient as a function of the monitored cardiac parameter.

8. A medium according to claim 7, the instructions further causing the processor to take a remedial action in response to the monitoring of the cardiac parameter.

9. A medium according to claim 8, wherein the instructions causing the processor to take remedial action comprises instructions causing the processor to perform at least one of:

delivering pacing stimuli to the heart;

delivering a drug to the patient;

controlling a device to deliver therapy to the patient;

generating an alert.

10. A method according to claim 9, wherein generating an alert signal further comprises wirelessly communicating an alert to a remote transceiver unit.

11. A method according to claim 10, further comprising at least a one of:

uploading the pulmonary edema status of the patient to the remote transceiver unit;

downloading data or programming instructions to a patient transceiver unit.

12. A medium according to claim 8, the instructions further causing the processor to:

compare a change in the monitored cardiac parameter to a threshold; and take the remedial action when the monitored cardiac parameter surpasses the threshold.

13. A medium according to claim 7, the instructions further causing the processor to monitor at least one cardiac parameter over a second plurality of cardiac cycles.

14. A medium according to claim 7, the instructions further causing the processor to evaluate the monitored cardiac parameter to determine whether a change in the monitored cardiac parameter indicates a change in pulmonary edema.

15. A device comprising:

a sensor to sense electrical signals from a heart of a patient; and a processor to receive the electrical signals and to monitor a cardiac parameter over a plurality of cardiac cycles, wherein the cardiac parameter comprises at least one of:
an amplitude of a QRS complex generated by a heart;
an integral of the QRS complex,
an integral of a QRST segment and wherein the processor is further configured to monitor pulmonary edema in a body of a patient as a function of the cardiac parameter.

16. A device according to claim 15, further comprising:

at least one electrode disposed proximate to the heart; and an implantable pulse generator to deliver pacing therapy to the heart via the at least one electrode;

wherein the processor is further configured to control the implantable pulse generator as a function of the pulmonary edema.

17. A device according to claim 16, wherein in addition to the at least one electrode at least two other electrodes are disposed in electrical communication with the heart and further comprising:

means for taking multiple measurements between the at least one electrode and the at least two other electrodes for detecting pulmonary edema.

18. A device according to claim 17, wherein the means for taking multiple measurements further comprises for at least one of said measurements, mathematically integrating or mathematically deriving said at least one of said measurements to render a new metric of edema.

19. A device according to claim 17, wherein the means for taking multiple measurements further comprises for at least two of said measurements, means for comparing said at least two of said measurements to render a new metric of edema.

20. A device according to claim 17, further comprising:

means for performing data validation to determine whether a change in cardiac parameters or the new metric for edema is due to pulmonary edema or other factors.

21. A device according to claim 15, further comprising a drug pump to administer a drug to the patient, wherein the processor is further configured to control the drug pump as a function of the pulmonary edema.

22. A device according to claim 15, further comprising an output device to generate an alert, wherein the processor is further configured to control the output device as a function of the pulmonary edema.

23. A device according to claim 15, wherein the device is implanted in the body of the patient.

24. A device according to claim 15, wherein the device is external to the body of the patient.

25. A device according to claim 15, wherein the processor is further configured to evaluate the monitored cardiac parameter to determine whether a change in the monitored cardiac parameter indicates a change in the pulmonary edema.

26. A system comprising:

cardiac monitoring means to monitor at least one cardiac parameter over a plurality of cardiac cycles, the cardiac parameter comprising at least one of an amplitude of a QRS complex generated by a heart, an integral of the QRS complex, and an integral of a QRST segment; and fluid monitoring means to monitor pulmonary edema in a patient as a function of the monitored cardiac parameter.

27. A system according to claim 26, further comprising remedial means to take remedial action as a function of the pulmonary edema.

28. A system according to claim 27, wherein the remedial means comprises at least one of:

an implantable pulse generator means to deliver pacing therapy to a heart;

a drug pump means to administer a drug to the patient;

an output device means to generate an alert.

* * * * *